United States Patent [19]

Bolduc et al.

[11] 4,109,654
[45] Aug. 29, 1978

[54] SINGLE STROKE DISPENSING APPARATUS

[75] Inventors: Lee R. Bolduc, St. Petersburg, Fla.; Eugene A. Dickhudt, New Brighton, MN

[73] Assignee: Population Research, Inc., Clearwater, Fla.

[21] Appl. No.: 713,294

[22] Filed: Aug. 10, 1976

[51] Int. Cl.$^2$ .............................................. A61M 1/00
[52] U.S. Cl. ...................................... 128/235; 128/1R
[58] Field of Search ............ 128/234, 235, 260, 349 B, 128/349 BV, 349 R, 1 R, 2 F, 127, 129

[56] References Cited

U.S. PATENT DOCUMENTS

| 3,422,813 | 1/1969 | Braley, Jr. et al. | 128/1 R |
| 3,680,542 | 8/1972 | Cimber | 128/1 R |

OTHER PUBLICATIONS

"The Effect of Methyl Cyanoacrylate Tissue Adhesive on the Human Fallopian Tube and Endometrium" by Stevenson et al., The Journal of Obstetrics and Gynaecology of the British Commonwealth, Nov. 1972, vol. 79, pp. 1028-1039.

Primary Examiner—John D. Yasko

[57] ABSTRACT

A material dispensing apparatus for placing a material in the uterine cavity and moving the material from the uterine cavity into the fallopian tubes of a female. An elongated probe carries an expandable member, and a housing connected to the probe has a piston and cylinder structure and a container for storing the material. Material and expansion drive mechanisms are connected to a single actuator selectively controllable by an operator. When the actuator is operated it is moved into the housing to both dispense the material and expand the expandable member. Pressure control means are provided in the drive linkage for expanding the expandable member to assure that a predetermined maximum pressure is not surpassed. The operator may fully depress the actuator and the pressure control means will both determine the maximum pressure and substantially maintain that pressure should a leak occur. Additional pressure control means are provided in the cylinder structure to compensate for atmospheric pressue change and to coordinate the balloon expansion relative to the material dispensing. Means are also provided in the material dispensing drive linkage to prevent the dispensed material from flowing back into its container when maximum pressure is applied. A replaceable probe portion is provided in the preferred embodiment.

20 Claims, 8 Drawing Figures

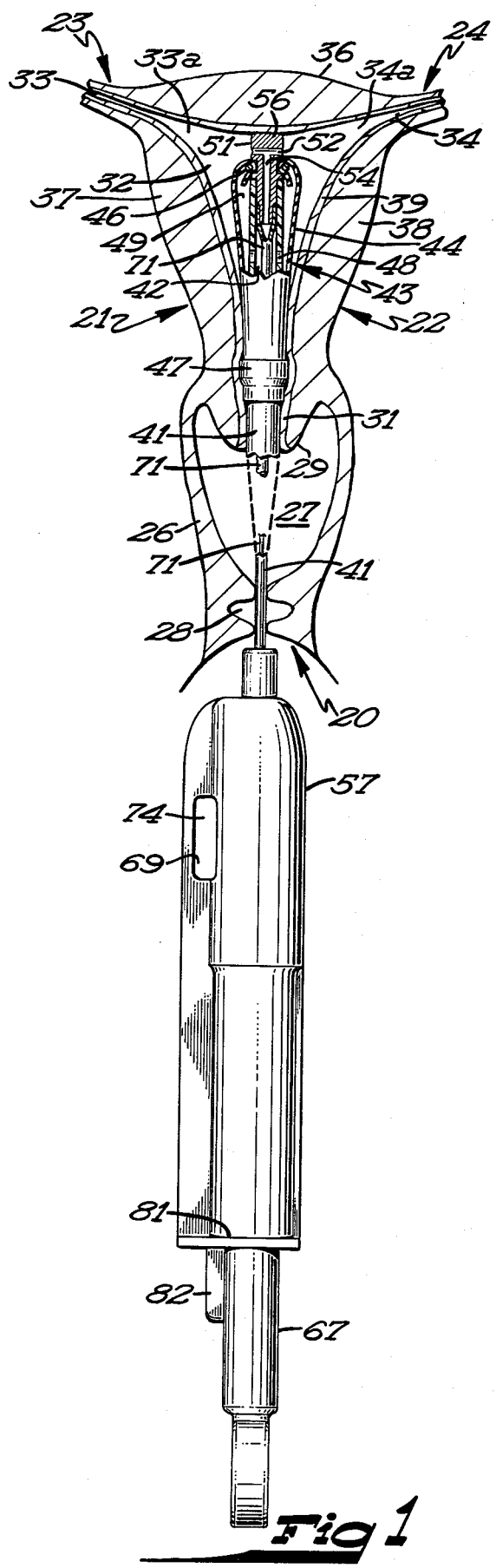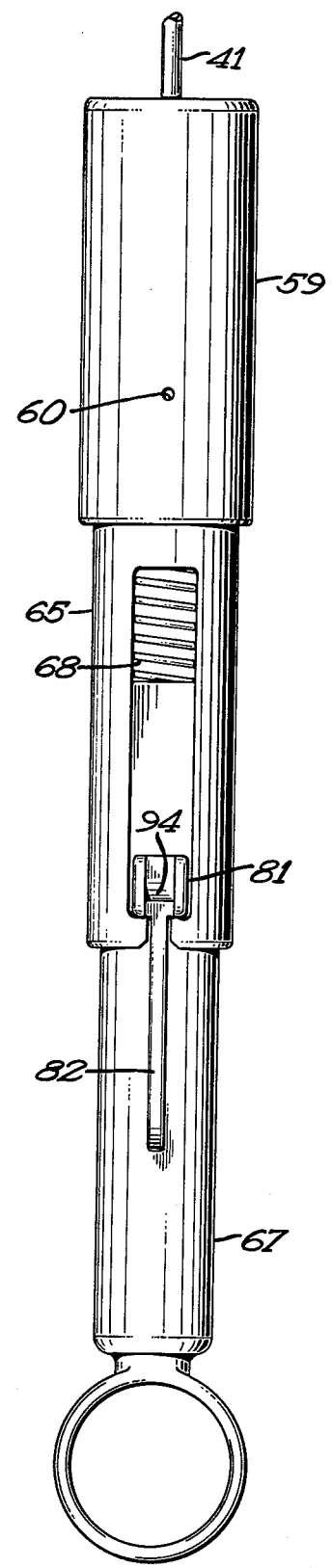

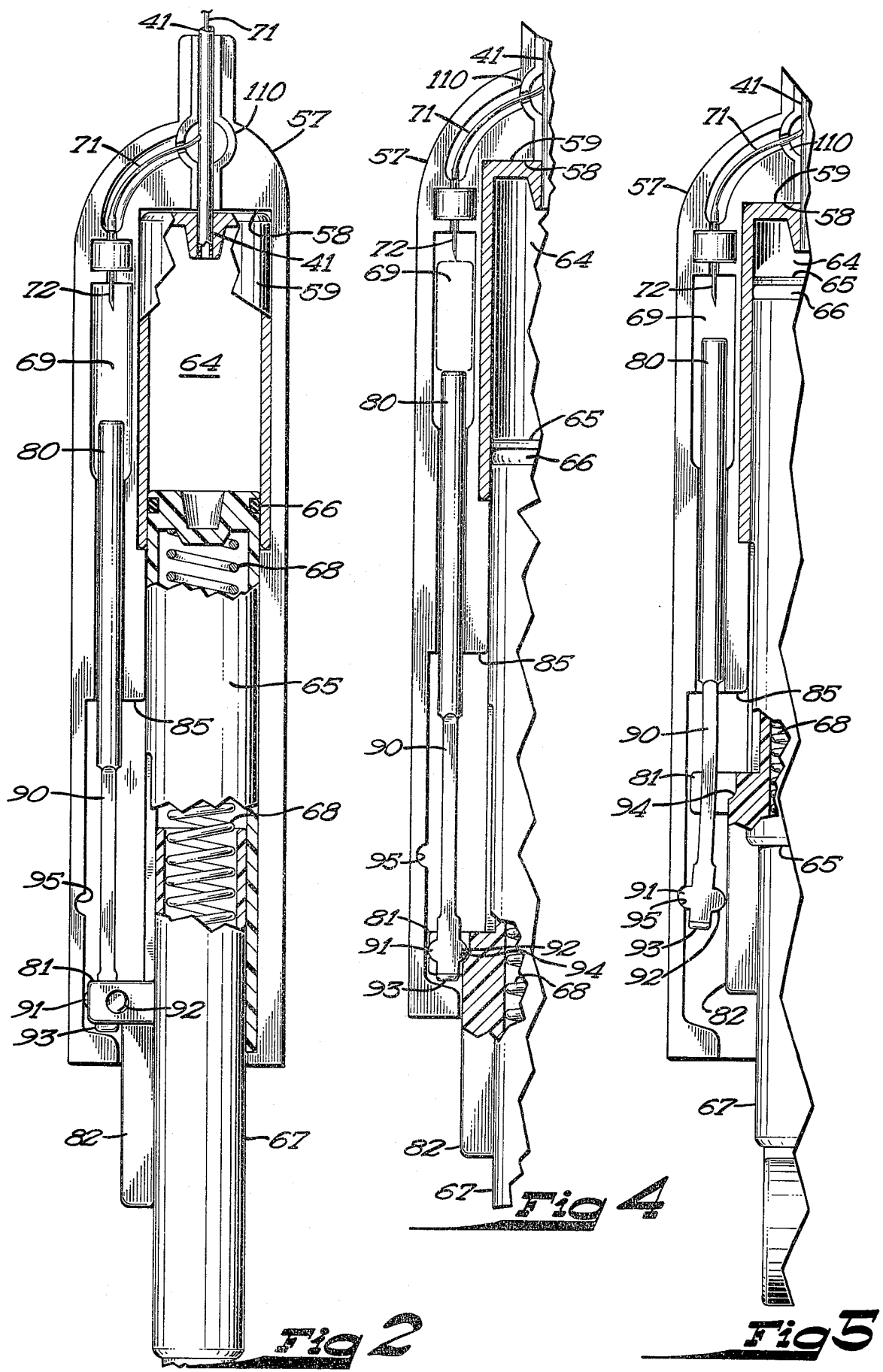

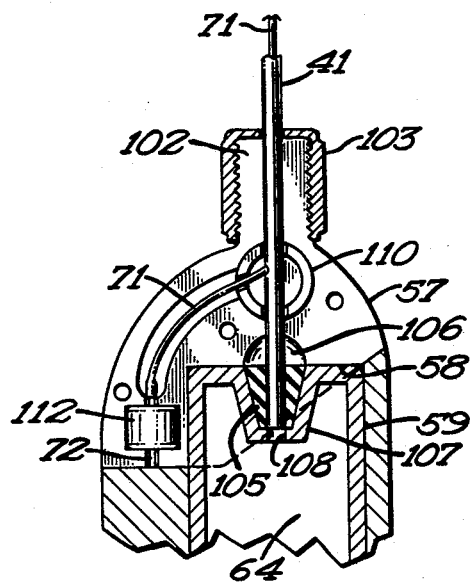
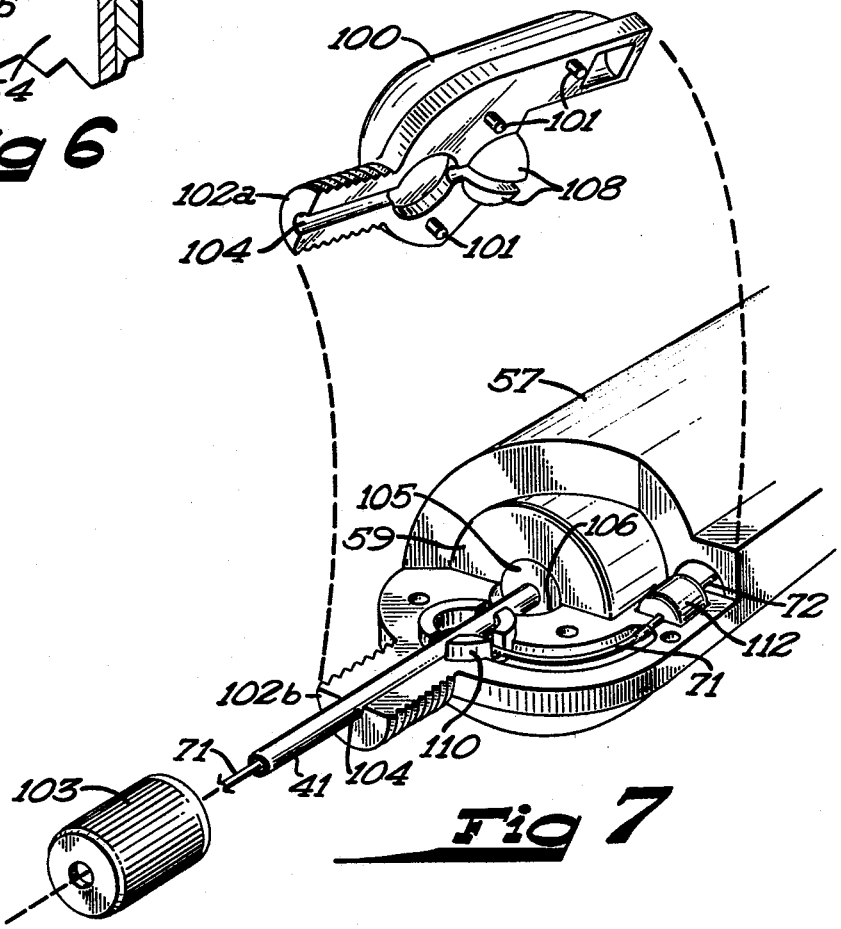
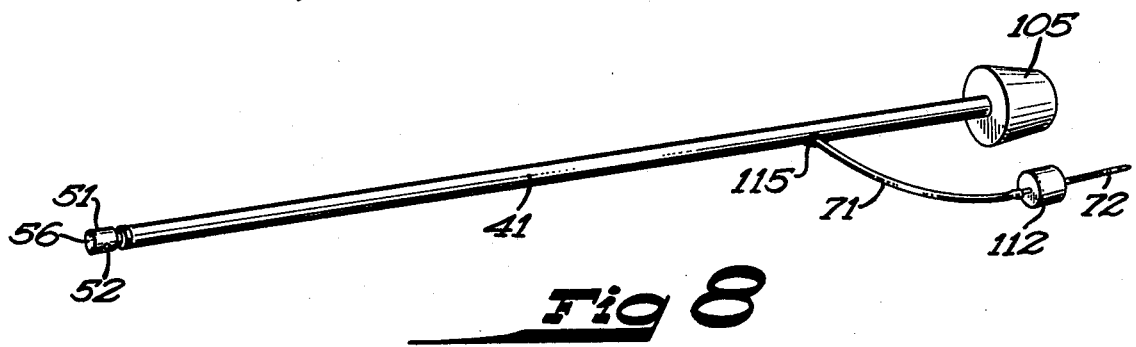

SINGLE STROKE DISPENSING APPARATUS

BACKGROUND OF THE INVENTION

Apparatus for dispensing materials into the Fallopian tubes of a female through non-surgical procedures have been described in a plurality of patents issued to the inventors of this invention, including U.S. Pat. No. 3,875,939, entitled "Single Stroke Dispensing Method", issued Apr. 8, 1975, which is herein incorporated by reference in its entirety.

Through the use of such dispensing apparatus, liquid tissue adhesives are injected into the Fallopian tubes to occlude the canals of the tubes. The materials used for this purpose are generally sensitive to moisture. Therefore, these materials will quickly set up in the uterine cavity, if not quickly forced into the canals of the Fallopian tubes. This motion of the materials is done by the rapid expansion of a member which fills the uterine cavity, thus applying pressure to the materials to force them into the Fallopian tubes. It has been found that high pressures cannot be used to rapidly inject the tissue adhesive into the canals as the material may then be forced through the Fallopian canals into the body cavity, or through the walls of the uterus into the blood stream, or that the walls of the uterine cavity may, in fact, be ruptured. It is thus necessary to provide for a control of maximum pressure and an improved means for accomplishing this control is described herein. Further, once the maximum pressure is reached, it is advantageous to maintain that pressure should it be subject to change, for example due to expansion of the walls of the uterus or to the flow of the materials leaving the uterine cavity. The improved apparatus of this invention not only provides control to avoid exceeding the maximum pressure, but provides a pressure regulation to maintain the pressure substantially constant throughout the dispensing operation. A further improvement of this invention prevents retro-flow of the materials when they are placed under pressure. A still further improvement provides for a replaceable probe portion to be used with the same control portion of this invention.

SUMMARY OF THE INVENTION

This invention is directed to an apparatus for dispensing material into both canals of the Fallopian tubes of a female primate, and to apparatus for controlling and regulating the pressure under which the materials are dispensed into the Fallopian tubes. More specifically, the invention is directed to an apparatus for introducing a predetermined amount of tissue adhesive into the canals of the Fallopian tubes of a female primate from the uterine cavity. The apparatus has an elongated probe having a forward end carrying an expandable balloon-like assembly. A dispensing housing having a single actuator is used to expand the balloon assembly and to discharge the materials into the uterine cavity. The dispenser has a first drive assembly operable to initially partially expand the balloon-like assembly to form a seal and holding structure in the lower portion of the uterine cavity. Continued movement of the actuator discharges the material into the uterine cavity above the partially expanded balloon-like assembly. As the actuator continues to move, the balloon assembly expands to fully displace the uterine cavity and thus forces the fluids into both Fallopian tubes. The sequence of events is accomplished by a single stroke actuation of the actuator by an operator who moves the actuator merely from one position to another.

The first drive assembly includes pressure control means, more specifically a low rate bias means or spring, which both prevents the pressure in the uterine cavity from exceeding a maximum amount, and regulates the pressure to avoid a detrimental pressure drop. As used herein, and as will be recognized by those familiar with the science of springs, the term low rate spring comprises a spring having a low change of force during compression. The spring of this invention is provided with a length significantly greater than the distance to be compressed, for example at least two to one, to further reduce the change of force due to compression. The apparatus includes a second drive assembly for dispensing the material which, in turn, includes apparatus for preventing retro-flow of the material, that is, it is prevented from returning to its original container when under pressure. Atmospheric vent means are provided in the first drive assembly which in addition to compensating for changes in atmospheric pressure, provide coordination to assure the balloon-like assembly does not expand too much before the materials enter the uterine cavity. Both the first and second drive assemblies are completely operated in proper sequence by the single actuator.

The invention also includes replaceable probes for use with a single control housing, which provides significant cost savings.

IN THE DRAWINGS

FIG. 1 is a foreshortened sectional view of a reproductive system of a female primate accomodating a dispensing instrument of the apparatus of this invention for dispensing fluids into both Fallopian tubes;

FIG. 2 is a longitudinal sectional view of the dispensing assembly of the apparatus of this invention;

FIG. 3 is a side longitudinal view of a portion of the apparatus of FIG. 2, which portion comprises the expansion drive assembly of this invention;

FIG. 4 is a longitudinal view of another portion of the apparatus of FIG. 2 showing a first position of the material dispensing drive assembly portion of this invention;

FIG. 5 is a view similar to that of FIG. 4 showing the material dispensing drive assembly in a second position;

FIG. 6 is a sectional view of a portion of the apparatus of FIG. 1 showing a replaceable probe apparatus;

FIG. 7 is an exploded view showing further details of the apparatus of FIG. 6; and FIG. 8 is a view of the replaceable probe.

DESCRIPTION OF THE PREFERRED EMBODIMENT

Referring to the drawings, there is shown in FIG. 1 the dispensing apparatus of this invention indicated generally at 20, the apparatus having its probe located in the uterine cavity of a female primate. The female primate reproductive system shown generally at 21 includes a uterus 22 joined to a pair of Fallopian tubes 23 and 24. The lower part of uterus 22 is integral with an elongated vagina 26. Vagina 26 has a vaginal cavity 27 including an opening, or entrance 28. The opposite end of vaginal cavity 27 is in communication with the cervix 29 which in turn has a cervical opening 31 providing a passage from the vaginal cavity 27 to the uterine cavity 32. Fallopian tubes 23 and 24 open, or have exits, 33A and 34A, to opposite sides of the upper part of the uterine cavity 32. A uterus such as 22 is a generally pearshaped, thick-walled, hollow organ situated between the bladder and the rectum. It is well known that the uteri of female primates may vary greatly in size and shape, wall thickness, wall strength, and sensitivity to pain. Therefore, the depiction of uterine cavity 32 as being triangular in shape is merely a generalization for the purposes of this disclosure. Fallopian tubes 23 and 24 are paired, trumpet-shaped, muscular members approximately 12 cm in length, that extend from the superior angles of uterine cavity 32 to the female ovaries (not shown). Outlets 33A and 34A of canals 33 and 34, respectively, can vary in position relative to the uterine cavity and relative to each other. Outlets 33A and 34A are most often symmetrically opposite each other, as shown in FIG. 1, and their position and proximity are principally related to the size and configuration of the uterus. It is well known that the size of canals 33 and 34 and the size of outlets 33A amd 34A will vary from female to female.

Fallopian tubes are divided into isthmus, intramural, and ampullary sections. Canals 33 and 34 provide passages for the movement of ova from the ovaries to the uterine cavity 32, as well as the movement of sperm from the uterine cavity toward the ovaries. The intramural sections of the Fallopian tubes traverse the uterine wall generally in a more or less straight fashion, but their course may be tortuous in some females. The walls of the Fallopian tubes consist of three layers including the serosal layer, the muscular layer, and the mucosal lining.

In FIG. 1, uterus 22 is shown as having a top wall or fundus 36 and side walls 37 and 38 which surround the uterine cavity 32. The inside of fundus 36 and the insides of side walls 37 and 38 have a lining or membrane 39 which is periodically sloughed off in the normal cycle of the female.

The placement of a desired fluid into the Fallopian tubes of a female may either open or close the tubes to either facilitate or prevent pregnancy. Apparatus for non-surgically dispensing the desired fluid and assuring that it enters both Fallopian tubes, such as that described in prior art patents by the inventors of this invention, including U.S. Pat. No. 3,875,939 which has been incorporated by reference herein, must be able to function within the physical parameters defined above and to operate safely and surely in the uterine cavity regardless of its size or shape.

Referring again to FIG. 1, it is disclosed that a dispensing instrument 20 has an elongated probe or tubular member 41 with a length sufficient to pass through the vaginal cavity 27 and into the uterine cavity 32. In FIG. 1, the upper portion of probe 41 has been enlarged, for purposes of clarity of the drawings. Member 41 has a longitudinal passage 42 extending throughout its length. A balloon assembly, indicated generally at 43, is mounted on the upper or outer end of member 41. Balloon assembly 43 has a flexible and expandable sleeve member 44 surrounding the upper end of probe 41. A fastener 46, such as a collar or thread, provides the attachment of sleeve 44 to probe 41. Another fastener 47 attaches the opposite end of sleeve 44 to probe 41. Probe 41 has a plurality of openings 48 which provide communication between passage 42 and a chamber 49 within sleeve member 44.

Sleeve member 44 may be a tubular sheet member of soft and relaxed, flexible and elastic material, such as rubber or plastic, that expands with minimum tension. Preferably, the material used for member 44 has a low surface tension which allows uniform expansion under relatively low pressure. Member 44 will thus expand to fully displace uterine cavity 32 and conform to the shape of the uterine cavity without applying extreme pressures to localized portions of walls 37 and 38, or fundus 36.

The upper or outer end of probe 41 is closed with a head 51. Head 51 has a transverse passage 52 open to opposite sides of head 51. An elongated tube 71 is secured to head 51, and extends the length of probe 41. Tube 71, the upper portion of which has been expanded in the drawings for purposes of clarity, has a passage 54 for carrying a fluid material to the transverse passage 52 which in turn directs the fluid in opposite directions to create two portions in the upper section of uterine cavity 32. Head 51 has a cap 56 having a top surface or wall adapted to engage the fundus 36. Cap 56 spaces passage 52 from the inner wall of fundus 36.

Probe 41 is connected to a housing or body 57 which carries a cavity 69 for receiving a fluid container such as 74. A single stroke actuator 67 is connected to housing 57 to both control the expansion of balloon assembly 43 and the dispensing of fluids from container 74 through transverse passage 52.

Referring now to FIG. 2, it is seen that housing 57 includes a first cavity 58 which contains a cylinder 59 that has a cavity 64 through which fluid, such as air, is provided to probe 41 for the expansion of the balloon assembly. Cylinder 59 includes a vent hole 60. A piston member 65 including a piston ring 66 cooperates with cylinder 64 to force fluid into probe 41. Member 65 is tubular, and an actuator mechanism 67 is telescopically mounted within piston 65. A low rate spring member 68 is mounted within tubular member 65 and tubular actuator member 67, with spring member 68 being biased against the telescoping of actuator 67 into piston 65. Spring member 68 preferably has length at least twice as long as the distance it will be compressed. Member 67 is preferably vented (not shown) to the surrounding atmosphere to prevent a pressure build-up between it and member 65.

Members 59, 65, 67 and 68 form the essential portions of the balloon inflation drive assembly of the apparatus of this invention.

It can be seen that as actuator 67 is depressed into housing 57, the bias of spring 68 will cause piston 65 to move within cylinder 59, forcing air through probe 41 into the balloon assembly. Cylinder 59 is preferably lubricated with a substance such as silicon oil, to aid in the pumping process. When the pressure of the balloon assembly equals the pressure from spring 68, actuator 67 will continue to telescope into piston 65 due to the compression of spring 68, but because of the low rate of spring 68 piston 65 will not move to increase the pressure in the balloon assembly; thus the bias of low rate spring 68 creates a maximum pressure control for the balloon assembly.

Actuator 67 will continue to telescope into piston 65 against spring 68 until a member 81 attached to actuator 67 by a bar 82 strikes ledge 85 in housing 57. At that point, the operator of the apparatus merely holds actuator 67 at its fully depressed stopped position. Spring 68 will be compressed and maximum pressure will be in the balloon assembly. Should there be a drop of pressure at the balloon assembly, due for example to an expansion of the uterus or the displacement of some of the material which has left the uterine cavity to move into the Fallopian tubes, then spring 68 will expand force piston 65 further into cylinder 59 to return the pressure of the balloon assembly to maximum pressure. Thus, low rate spring 68 serves the function of pressure regulation by not allowing a significant drop of pressure of balloon assembly 43.

Vent hole 60 provides compensation for atmospheric changes. It will also be recognized that the placement of hole 60 along the length of cylinder 59 determines the time for expansion of sleeve member 44. That is, the farther piston member 65 must travel to reach hole 60, the later the expansion of sleeve member 44. Thus, vent hole 60 provides coordinate timing to assure that the materials enter uterine cavity 32 before sleeve member 44 has expanded more than desired. This will be understood further following the discussion below of the dual control by the single actuator.

From the above description of the operation of the significant portions of the expansion drive assembly mechanism of the apparatus of this invention, it becomes apparent that this invention provides both maximum pressure control and pressure regulation by utilizing a minimum number of parts.

Referring to FIG. 2, it is shown that housing 57 contains a second cavity 69. Tube 71 which is connected to transverse passage 52 of probe 41 terminates in a sharp, needle-like end 72 which extends into cavity 69. An actuator rod 80 is mounted in housing 57 and extends from cavity 69 to a contact with member 81. Cavity 69 is adapted to receive a material or chemical container or ampulla in a position such that pressure from forward movement of rod 80 will cause point 72 to puncture the ampulla and the continued forward movement of rod 80 will force the material from the ampulla through tube 71 and transverse passage 52 into the uterine cavity.

It can be seen in FIG. 2 that the movement of actuator 67, will, through bar 82 and member 81, cause the movement of rod 80 in proper sequence with the movement of the inflation drive assembly mechanisms. Rod 80, member 81 and member 82, in cooperation with a notch 95 in housing 57 comprise a significant portion of the material drive assembly mechanism of the apparatus of this invention, the operation of which will be more fully described in the discussions of FIGS. 3, 4, and 5 below.

To summarize the operation of the single actuator 67 of the apparatus as shown in FIG. 2, it will be recognized that the operator of the apparatus of this invention may merely depress the one actuator 67 to accomplish a pressure controlled and regulated inflation of the balloon assembly 43 as well as the properly timed dispensing of materials into the uterine cavity from a container adapted to be placed in cavity 69. After the operator has held actuator 67 in the depressed position for a short period of time, the entire process of placing materials in the Fallopian tubes of a female will be completed. The operator then need only withdraw actuator 67 from housing 57 to deflate balloon assembly 43, and may then remove the entire apparatus from communication with the body of the female.

Referring now to FIG. 3, there is shown a left side view of the inflation drive assembly as shown in FIG. 2. In FIG. 3, it can be seen that piston 65 has a slot which permits sliding of bar 82 and thus member 81, along the length of piston 65 as actuator 67 telescopes into piston 65. In FIG. 3, vent hole 60 can be seen as placed in cylinder 59.

For an understanding of the operation of the material drive assembly of the apparatus of this invention, reference will now be made to FIGS. 4 and 5. In FIG. 4, it can be seen that rod 80 includes a flexible portion 90 which terminates in a knob including a pair of bosses 91 and 92. The knob also includes a stop member 93. A portion of member 81 has been cut away in FIG. 4 to show that bar 82 includes a notched portion 94 adapted to cooperate with boss 92, and that the lower edge of bar 82 abuts with stop member 93.

It can be seen from FIG. 4 that as actuator 67 is depressed into housing 57, notch 94 will react to provide a forward and outward pressure on boss 92 causing rod 80 to move forward to perform its material dispensing function.

Referring now to FIG. 5, it can be seen that when the travel of rod 80 has gone a distance sufficient for boss 91 to reach notch 95, the outward pressure from bar 82 will cause portion 90 of rod 80 to flex, locking boss 91 in notch 95. This will stop the movement of chemical rod 80 which will at this point of movement have already completed its fluid dispensing operation.

In FIG. 5, it is apparent that the continued movement of actuator 67 after boss 91 has slipped into notch 95 will keep rod 80 in the locked position due to boss 92 riding on the outer edge of bar 82. The purpose of this locking action is to prevent dispensed materials from flowing back into container 74 as the pressure in the balloon assembly 43 increases due to the movement of actuator 67. That is, if rod 80 were free to move backwards after the fluid dispensing function is completed, the expansion of balloon assembly 43 might force a retro-flow of dispensed materials back through transverse passage 52 and probe 41, into the ampulla from which the fluid came. The mechanism of the material drive assembly as described in FIGS. 2, 3, 4 and 5 prevents this undesirable result.

When actuator 67 is withdrawn from housing 57, prior to removal of the dispensing apparatus from the female body, the realignment of notch 94 with box 92 will allow portion 90 of rod 80 to unflex, thus straightening rod 80 and removing boss 91 from its locking position in notch 95. Member 81 will now interact with member 93 to draw rod 80 down to its original position.

Referring now to FIGS. 6, 7 and 8, there is shown an embodiment of the invention including a replaceable probe and apparatus comprising an additional portion of housing 57 to facilitate removal and replacement of the probe. It can be seen that the replaceable probe comprises probe 41 terminating in a plug 105. Plug 105 is a truncated cone and is made of a material, such as rubber, which will have sealing properties when it is placed in a mating housing. Tube 71 is connected to probe 41 in the manner described above and to needle 72. Needle 72 is tightly fitted through a cylindrical support member 112.

Housing 57 is provided with a removable member 100, which bears a plurality of extending peg members 101 adapted to mate with aligned holes shown in housing 57. Member 100 also includes a member 102A adapted to mate with a member 102B on housing 57 to form a threaded female member 102. Member 102 includes a groove 104 for holding probe 41. A threaded male member 103 is provided which can be placed over probe 41 and threaded on to member 102 to hold member 100 in contact with housing 57. Other connection means could be used for members 102 and 103. For example, member 103 could be made of rubber to be slipped over and hold member 102 in place.

It can also be seen that cylinder 59 includes a housing 107 adapted to receive plug 105 such that probe 41 mates with an aperture 108 in member 107 to provide access between probe 41 and cavity 64 of cylinder 59. An access groove 106 is provided in housing 57 to facilitate the entry of plug 105 into housing 107. Member 100 is provided with a pair of ears 108 adapted to tightly fit into channel 106 on either side of probe 41 when member 100 is placed on housing 57. When thus placed, ears 108 will tightly hold plug 105 in housing 107. Housing 57 is also provided with a slotted tubular member 110 adapted to mate with a recess in member 100. A first pair of slots in member 110 allow probe 41 to be seated therein as it passes through channel 104 and an aperture in the top of male threaded member 103. A second slot in member 110 allows the passage therethrough of tube 71. It can also be seen that support member 112, which carries needle 72 is tightly held in housing 57 and member 100 by a mating pair of cylindrical slots, thus positioning and securely holding needle 72 against the force it receives during the chemical injection process. In FIG. 8 it can be seen that the outlet point of tube 71 from probe 41 is sealed by a suitable material 115 to prevent pressure leakage.

It should be recognized that in the non-replaceable probe embodiment of this invention, as shown for example, in FIG. 2, member 110 and the channel carrying tube 71 are preferably filled with an encapsulating material, such as a two-part epoxy, to hold the respective members of the invention securely.

From the above description, it can be seen that this embodiment of the invention provides a highly economical function of allowing a single housing and control unit to be used with a plurality of probe assemblies. It will be recognized that the particular apparatus shown for the purpose of allowing use of a replaceable probe can be varied in many ways without removing the basic concept of the apparatus.

What is claimed is:

1. In dispensing apparatus for dispensing materials into the Fallopian tubes of a female primate, including means for dispensing materials into the uterine cavity of the female primate, means for expanding within the uterine cavity for moving the dispensed materials from the uterine cavity into the Fallopian tubes, and means for controlling the means for dispensing materials and the means for expanding, improved means for controlling comprising: first drive assembly means for controlling the means for expanding; and the first drive assembly means including bias means for limiting maximum pressure of the means for expanding and for substantially regulating the pressure of the expansion means.

2. The apparatus of claim 1 in which the bias means comprises a single spring means.

3. The apparatus of claim 2 in which the spring means comprises a low rate spring.

4. The apparatus of claim 3 in which the length of the low rate spring is significantly greater than the distance of compression of the spring required to control the means for expansion.

5. The apparatus of claim 1 including: second drive assembly means for controlling the means for dispensing materials; the second drive assembly means including means for preventing retro-flow of dispensed materials under pressure.

6. The apparatus of claim 5 including: actuator means for simultaneously actuating the first and second drive assembly means.

7. The apparatus of claim 6 in which the actuator means comprises a single actuator means for actuating the full drive cycles of the first and second drive assembly means with a single stroke.

8. The apparatus of claim 6 including pressure means in the first drive means for further coordination of timing between the first and second drive means.

9. The apparatus of claim 8 in which the pressure means comprises vent means.

10. The apparatus of claim 6 in which: the means for preventing retro-flow includes means for cooperating with the actuator means for locking the second drive assembly means at a predetermined position when the desired amount of materials have been dispensed.

11. The apparatus of claim 6 including: housing means for the first and second drive assembly means, and the actuator means; and the housing means including means for receiving materials-carrying ampula means.

12. The apparatus of claim 11 in which the means for preventing retro-flow comprises: rod means for engaging ampula means to force materials through the means for dispensing materials; means mounting the rod means for linear travel in the housing means; the rod means having a rigid portion at one end for engaging the ampula means, and having a flexible portion at the other end including first and second extending means; the actuator means including force means for releasably engaging the first extending means; the housing having catch means for releasably engaging the second extending means, such that movement of the actuator means causes the force means to engage the first extending means to move the rod until the second extending means reaches and is flexed into engagement with the catch means; and the force means thereafter sliding along the flexible portion of the rod means to lock the rod means.

13. The apparatus of claim 1 including: means for selectively removing and replacing any one of a plurality of the means for expanding and a portion of the means for dispensing, from connection with the control means.

14. In dispensing apparatus, including probe means having first and second channel means, material dispensing means connected to one end of the first channel means, expansion means connected to one end of the second channel means, housing means carrying material dispensing control means and expansion control means, the improvement comprising: means for selectively connecting the probe means to the housing means, the other end of the first channel means to the material dispensing control means, and the other end of the second channel means to the expansion control means.

15. The apparatus of claim 14 in which: the dispensing control means includes means for preventing retro-flow of dispensed materials.

16. The apparatus of claim 15 including: a single actuator means for actuating both said control means.

17. The apparatus of claim 16 in which the means for preventing retro-flow includes: rod means for engaging ampula means to force materials through the first channel means and the material dispensing means; the rod means mounted for linear travel in the housing means and having a rigid portion at a first end for engaging the ampula means and having a flexible portion at a second end; the flexible portion including first and second extending knobs; the actuator means including carriage means for releasably engaging the first knob; the housing having catch means for releasably engaging the second knob, such that movement of the actuator means causes the carriage means to engage the first knob to move the rigid portion against the ampula means until the second knob reaches the catch means and the flexing of the flexible portion causes the first knob to disengage from the carriage means; and the carriage means thereafter sliding along the flexed portion of the rod means to lock the rod means in position to prevent retro-flow until the actuator means is returned to its original position.

18. The apparatus of claim 14 in which the expansion control means includes: means for regulating the pressure of the expansion means.

19. The apparatus of claim 18 in which the means for regulating includes a single low rate spring.

20. The apparatus of claim 16 in which: the expansion control means includes vent means for controlling atmospheric pressure and for controlling the timing between the expansion and dispensing control means.

* * * * *